United States Patent
Wachi et al.

(10) Patent No.: US 9,295,660 B2
(45) Date of Patent: Mar. 29, 2016

(54) ANTIMALARIAL DRUG COMPRISING ALAREMYCIN OR DERIVATIVE THEREOF AS ACTIVE INGREDIENT

(75) Inventors: Masaaki Wachi, Tokyo (JP); Shigeharu Sato, London (GB); Tohru Tanaka, Tokyo (JP); Kiwamu Takahashi, Tokyo (JP)

(73) Assignees: Tokyo Institute of Technology, Tokyo (JP); SBI Pharmaceuticals Co., Ltd., Tokyo (JP)

( * ) Notice: Subject to any disclaimer, the term of this patent is extended or adjusted under 35 U.S.C. 154(b) by 172 days.

(21) Appl. No.: 13/883,038

(22) PCT Filed: Nov. 9, 2011

(86) PCT No.: PCT/JP2011/006273
§ 371 (c)(1),
(2), (4) Date: May 2, 2013

(87) PCT Pub. No.: WO2012/063487
PCT Pub. Date: May 18, 2012

(65) Prior Publication Data
US 2013/0217913 A1 Aug. 22, 2013

(30) Foreign Application Priority Data
Nov. 10, 2010 (JP) ................................. 2010-251562

(51) Int. Cl.
| | | |
|---|---|---|
| A61K 31/197 | (2006.01) | |
| A61K 31/16 | (2006.01) | |
| A61K 31/221 | (2006.01) | |
| A61K 9/00 | (2006.01) | |
| A61K 9/107 | (2006.01) | |
| A61K 9/20 | (2006.01) | |

(52) U.S. Cl.
CPC ............ *A61K 31/197* (2013.01); *A61K 9/0019* (2013.01); *A61K 9/107* (2013.01); *A61K 9/2018* (2013.01); *A61K 9/2027* (2013.01); *A61K 31/16* (2013.01); *A61K 31/221* (2013.01)

(58) Field of Classification Search
None
See application file for complete search history.

(56) References Cited

FOREIGN PATENT DOCUMENTS

| JP | 38-2798 | 3/1963 |
| JP | 2006-282577 | 10/2006 |

OTHER PUBLICATIONS

Heinemann, Structure of the Heme Biosynthetic Pseudomonas aeruginosa Porphobilinogen Synthase in Complex with the Antibiotic Alaremycin, Antimicrobial Agents and Chemotherapy, 2010, 54(1), pp. 267-272.*

Sato, Enzymes for Heme Biosynthesis are Found in Both the Mitochondrion and Plastid of the Malaria Parasite Plasmodium falciparum, Protist, 2004, 155, pp. 117-125.*
White, The Treatment of Malaria, The New England Journal of Medicine, 1996, 335(11), pp. 800-806.*
Awa et al., "Isolation of a New Antibiotic, Alaremycin, Structurally Related to 5-Aminolevulinic Acid from *Streptomyces sp.* A012304," Biosci. Biotechnol. Biochem., 69(9), pp. 1721-1725, 2005.
Frankenberg et al., "Cloning, Mapping and Functional Characterization of the hemB Gene of Pseudomonas Aeruginosa, which Encodes a Magnesium-Dependent 5-Aminolevulinic Acid Dehydratase," Mol. Gen. Genet, 257, pp. 485-489, 1998.
Fry et al., "Effect of Mitochondrai Inhibitors on Adenosinetriphosphate Levels in Plasmodium Falciparum," Comp. Biochem., Physiol., vol. 96B, No. 4, pp. 775-782, 1990.
Fry et al., "Site of Action of the Antimalarial Hydroxynaphthoquinone, 2-[trans-4-(4'-Chlorophenyl) Cyclohexyl]-3-Hydroxy-1, 4-Naphthoquinone (566C80)," Biochemical Pharmacology, vol. 43, No. 7, pp. 1545-1553, 1992.
Heinemann et al., "Structure of the Heme Biosynthetic *Pseudomonas aeruginosa* Porphobilinogen Synthase in Complex with the Antibiotic Alaremycin," Antimicrobial Agents and Chemotherapy, vol. 54, No. 1, pp. 267-272, Jan. 2010.
Jaffe, "Porphobilinogen Synthase, The First Source of Heme's Asymmetry," Journal of Bioenergetics and Biomembranes, vol. 27, No. 2, pp. 169-179, 1995.
Kervinen et al., "Mechanistic Basis for Suicide Inactivation of Porphobilinogen Synthase by 4,7-Dioxosebacic Acid, an Inhibitor that Shows Dramatic Species Selectivity," Biochemistry, 40, pp. 8227-8236, 2001.
Painter et al., "Specific Role of Mitochondrial Electron Transport in Blood-Stage Plasmodium Falciparum," Nature, vol. 446, pp. 88-91, Mar. 2007.

(Continued)

*Primary Examiner* — San-Ming Hui
*Assistant Examiner* — Andrew Lee
(74) *Attorney, Agent, or Firm* — Margaret B. Brivanlou; Leslie A. Serunian; King & Spalding LLP

(57) ABSTRACT

Provided is a preventive and/or therapeutic agent for malaria, comprising, as an active ingredient, 5-acetamido-4-oxo-5-hexenoic acid (Alaremycin) or a derivative thereof. A preventive and/or therapeutic agent for malaria is used which comprises, as an active ingredient, Alaremycin or a derivative thereof represented by formula (I) (wherein $R^1$ represents a hydroxy group, an amino group, or a substituted or unsubstituted straight chain or branched alkoxy group or alkylamino group having 1 to 8 carbons; $R^2$ represents hydrogen, a substituted or unsubstituted straight chain or branched alkyl group having 1 to 8 carbons, or a substituted or unsubstituted aromatic group having 4 to 10 carbons; and $R^3$ represents hydrogen or a methyl group).

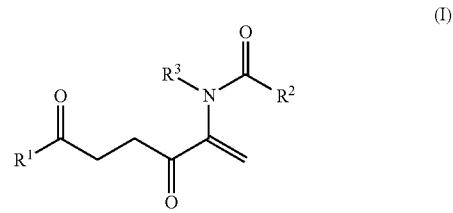

(I)

13 Claims, No Drawings

(56) References Cited

OTHER PUBLICATIONS

Phillips et al., "Plasmodium Dihydroorotate Dehydrogenase: a promising Target for Novel Anti-Malarial Chemotherapy," Infect. Disord. Drug Targets, 10(3), pp. 226-239, 2010.

Sato et al., "The Genome of Plasmodium Falciparum Encodes an Active δ- aminolevulinic acid dehydratase," Curr. Genet., 40, pp. 391-398, 2002.

Senior et al., "Comparative Studies on the 5-aminolaevulinic Acid Dehydratases from Pisum Sativum, *Escherichia Coli* and *Saccharomyces Cerevisiae*," Biochem. J., 320, pp. 401-412, 1996.

Surolia et al., "De Novo Biosynthesis of Herne Offers a New Chemotherapeutic Target in the Human Malarial Parasite," Biochemical and Biophysical Research Communications, vol. 187, No. 2, pp. 744-750, 1992.

Wachi et al., "Irregular Nuclear Localization and Anucleate Cell Production in *Escherichia coli* Induced by a $Ca^{2+}$ Chelator, EGTA," Biochimie, 81, pp. 909-913, 1999.

Iwai et al., "Synthesis and Antibacterial Activity of Alaremycin Derivatives for the Porphobilinogen Synthase," Bioorganic & Medicinal Chemistry Letters, vol. 21, No. 10, pp. 2812-2815, Mar. 28, 2011.

Tokyo Institute of Technology, et al., Extended European Search Report for European Patent Application No. 11840434.2, European Patent Office, Mar. 13, 2014, 7 pages.

Awa et al., "Isolation of a New Antibiotic, Alaremycin, Strucutally Related to 5-Aminolevullinic Acid from Streptomycese sp. A012304," Biosci. Biotechnol. Biochem., 69(9), pp. 1721-1725, 2005.

Frankenberg et al., "Cloning, Mapping and Functional Characterization of the hemB Gene of Pseudomonas Aeruginosa, which Encodes a Magnesium-Dependent 5-Aminolevulinic Acid Dehydratase," Mol. Gen. Genet., 257, pp. 485-489, 1998.

* cited by examiner

ANTIMALARIAL DRUG COMPRISING ALAREMYCIN OR DERIVATIVE THEREOF AS ACTIVE INGREDIENT

TECHNICAL FIELD

The present invention relates to an antimalarial drug useful for the prevention and/or treatment of an infection caused by malaria parasites, and more specifically relates to a preventive and/or therapeutic agent for malaria comprising 5-acetamido-4-oxo-5-hexenoic acid (Alaremycin) or a derivative thereof as an active ingredient.

BACKGROUND ART

Malaria is an infection caused by malaria parasites transmitted by Anopheles, and is an infection most feared by human beings since recorded history particularly in tropical and semitropical regions. The number of infected people once decreased by specific medicines such as quinine and chloroquine; however, drug-resistant parasites began to be discovered in the late 1950s and it is said that 3 to 5 hundreds of millions of people are still annually infected with the reemerging infectious disease and people totaling between 1 and 2 million die thereof. Although many other infectious diseases are treated or prevented with vaccines, for example, smallpox has been completely eradicated thereby, it is said that for malaria it would be essentially difficult to develop a vaccine since even a clue to develop the vaccine is not found despite that many researches have been conducted, probably because it is an infectious disease caused by parasites and has a complex life cycle.

Many researches are also conducted on the development of new drugs and the mechanism of drug resistance; however, a sense of crisis is expressed because more parasites having acquired drug resistance are found. Existing antimalarial drugs generally have strong side effects and cannot be prophylactically used in infested areas. The development of a new drug also poses a big economic problem since it is extremely expensive.

In 2005, Awa et al. discovered "Alaremycin" which was an antibiotic substance with a new structure found to have an antibacterial activity against *Escherichia coli* from a culture medium in which *Streptomyces* sp. strain A012304 grows by screening using the release of anucleate cells resulting from the inhibition of chromosome partitioning as a detection index (Non-patent Document 1) and was represented by formula (A) below:

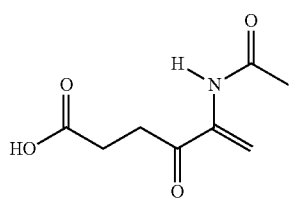

(A)

(Non-patent Document 2).

Alaremycin was demonstrated to act as an inhibitor of porphobilinogen synthase (PBGS) as a porphyrin/heme biosynthesis system enzyme synthesizing porphobilinogen (PBG) by use of 5-aminolevulinic acid (5-ALA) as a substrate (Non-patent Document 3). PBGS is divided into two types based on a difference in a metal ion serving as a cofactor: one is a $Zn^{2+}$ type distributed in cells of human and other animals and many bacteria and the other is a $Mg^{2-}$ type distributed in plant cells and some bacteria such as *Pseudomonas aeruginosa* (Non-patent Documents 4, 5, and 6).

PBGS is involved in the synthesis of porphyrin and its related compounds indispensable for the survival of living organisms, and its inhibitor, Alaremycin, has antibacterial activities against not only *Escherichia coli* used for the screening of producing bacteria but also *Pseudomonas aeruginosa* causing opportunistic infection in hospitals and problematical as a multiple-drug-resistant bacteria (Non-patent Document 3). The PBGS of *Pseudomonas aeruginosa* is PBGS of the $Mg^{2+}$ type, which is different in the structure from that of humans; thus, PBGS of the $Mg^{2+}$ type can probably be an effective target molecule in view of an antibacterial agent.

The acid amide (compound) of Alaremycin represented by formula (B) below is known as the anticancer antibiotic Primocarcin (Non-patent Document 7). The methyl ester (compound) of Alaremycin represented by formula (C) below is also known as a photosensitizer for the photo-dynamic therapy of cancer (Patent Document 1).

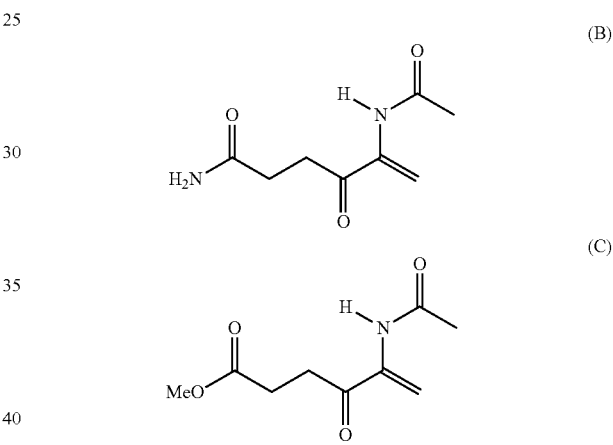

Heme proteins such as cytochrome c are present in the mitochondria of human malaria parasites as with humans, yeast and the like, and constitute an electron transport system; however, it is an established theory that the synthesis of ATP in parasites infecting, and proliferating in red blood cells approximately 100% depends on the extremely strong glycolytic system thereof and the involvement of mitochondria is almost negligible in terms of the ATP synthesis (Non-patent Document 7). However, it is known that malaria parasites have PBGS of the $Mg^{2+}$ type and perform the de novo synthesis of heme despite surviving by ingesting a large amount of hemoglobin (Non-patent Documents 8 and 9).

However, the action mechanism of Atovaquone as an antimalarial agent already put to practical use as a pharmaceutical agent is to specifically inhibit a cytochrome bc1 complex (complex III) present in the mitochondrial membrane of human malaria parasites (Non-patent Document 10). This suggests that the electron transport system of mitochondria is essential for the proliferation of parasites.

The reason is unclear in many points why mitochondria necessitates the electron transport system despite the unnecessity of ATP synthesis; however, it is suggested that the system acts by transferring electrons released when dihydroorotic acid dehydrogenase as one of the enzymes in the pyrimidine synthesis system reduces dihydroorotic acid to make orotic acid, to cytochrome c oxidase via ubiquinone and cytochrome c (Non-patent Document 11). In addition, it is known that malaria parasites cannot utilize host-derived pyrimidine (Non-patent Document 12).

PRIOR ART DOCUMENTS

Patent Documents

Patent Document 1
Japanese unexamined Patent Application Publication No. 2006-282577

Non-Patent Documents

Non-patent Document 1
Biochimie, 1999, 81, 909-913.
Non-patent Document 2
Biosci. Biotechnol. Biochem., 2005, 69, 1721-1725.
Non-patent Document 3
Antimicrob. Agents Chemother., 2010, 54, 267-272.
Non-patent Document 4
J. Bioenerg. Biomembr., 1995, 27, 169-179.
Non-patent Document 5
Biochem. J., 1996, 320, 401-412.
Non-patent Document 6
Mol. Gen. Genet., 1998, 257, 485-489.
Non-patent Document 7
Comp. Biochem. Physiol., 1990, B 96, 775-782
Non-patent Document 8
Curr. Genet., 2002, 40, 391-398.
Non-patent Document 9
Biochem. Biophys. Res. Comm., 1992, 187, 744-750.
Non-patent Document 10
Biochem. Pharmacol., 1992, 43, 1545-1553.
Non-patent Document 11
Nature, 2007, 446, 88-91.
Non-patent Document 12
Infect. Disord. Drug Targets., 2010, 10, 226-239.

SUMMARY OF THE INVENTION

Object to be Solved by the Invention

There is need for the development of an economically excellent antimalarial drug which is truly effective, has few side effects, and less easily produces resistant parasites. An object of the present invention is to provide an antimalarial drug comprising 5-acetamido-4-oxo-5-hexenoic acid (Alaremycin) or a derivative thereof as an active ingredient, useful for the prevention and/or treatment of malaria, and a preventive and/or therapeutic method using the same.

Means to Solve the Object

The present inventors have closely traced the action mechanism of an antimalarial drug represented by quinine, chloroquine, or Atovaquone, research on resistance to these antimalarial drugs, and the like, and conceived that the inhibition of PBGS by Alaremycin probably produces the loss of function of a series of heme proteins such as cytochrome c, causes the failure of the electron transport system of mitochondria, makes the pyrimidine synthesis system down to markedly inhibit nucleic acid synthesis and protein synthesis, and suppresses the proliferation of malaria parasites. The suppression of the proliferation of malaria parasites parasitic in red blood cells will result in the disappearance of malaria parasites due to the turnover of red blood cells.

For the therapy of falciparum malaria by Atovaquone alone, recrudescence due to the mutation of cytochrome b gene often occurs; however, the present invention can overcome this weakness. These intensive studies have at last resulted in accomplishing the present invention.

Thus, the present invention relates to:

(1) a preventive and/or therapeutic agent for malaria, comprising Alaremycin or a derivative thereof represented by formula (I):

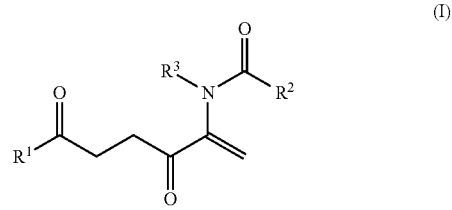

(wherein $R^1$ represents a hydroxy group, an amino group, or a substituted or unsubstituted straight chain or branched alkoxy group or alkylamino group having 1 to 8 carbons; $R^2$ represents hydrogen, a substituted or unsubstituted straight chain or branched alkyl group having 1 to 8 carbons, or a substituted or unsubstituted aromatic group having 4 to 10 carbons; and $R^3$ represents hydrogen or a methyl group), or a pharmaceutically acceptable salt thereof as an active ingredient.

The present invention also relates to:

(2) the preventive and/or therapeutic agent for malaria according to (1) above, wherein $R^1$ represents a hydroxy group; $R^2$ represents a methyl group; and $R^3$ represents hydrogen;

(3) the preventive and/or therapeutic agent for malaria according to (1) above, wherein $R^1$ represents a methoxy group; $R^2$ represents a methyl group; and $R^3$ represents hydrogen; and (4) the preventive and/or therapeutic agent for malaria according to (1) above, wherein $R^1$ represents an amino group; $R^2$ represents a methyl group; and $R^3$ represents hydrogen.

In another embodiment, the present invention relates to a preventive and/or therapeutic method for malaria, comprising administering a pharmaceutical comprising Alaremycin or a derivative thereof represented by formula (I):

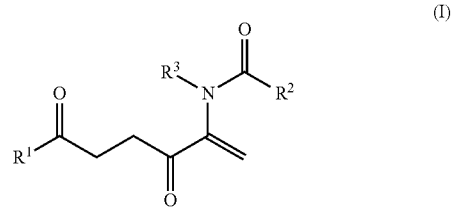

(wherein $R^1$ represents a hydroxy group, an amino group, or a substituted or unsubstituted straight chain or branched alkoxy group or alkylamino group having 1 to 8 carbons; $R^2$ represents hydrogen, a substituted or unsubstituted straight chain or branched alkyl group having 1 to 8 carbons, or a substituted or unsubstituted aromatic group having 4 to 10 carbons; and $R^3$ represents hydrogen or a methyl group), or a pharmaceutically acceptable salt thereof as an active ingredient, to a patient in need thereof, and a method for using Alaremycin or a derivative thereof represented by formula (I) or a pharmaceutically acceptable salt thereof for the prevention and/or treatment of malaria.

Effect of the Invention

Alaremycin or a derivative thereof according to the present invention is useful as a therapeutic and/or preventive agent for malaria.

MODE OF CARRYING OUT THE INVENTION

The alkyl moiety of the alkoxy group and alkylamino group having 1 to 8 carbons and the alkyl group having 1 to 8 carbons in the compound (I) may be straight chain or branched alkyl groups; specific examples thereof include a methyl group, an ethyl group, a propyl group, an isopropyl group, a butyl group, a sec-butyl group, a tert-butyl group, a pentyl group, an isopentyl group, a neopentyl group, a hexyl group, a heptyl group, and an octyl group. They may also be substituted or unsubstituted alkyl groups; specific examples of these substituents include 1) halogen atoms such as fluorine atom, chlorine atom, bromine atom, and iodine atom; 2) alkoxy groups such as methoxy, ethoxy, propoxy, and isopropoxy; 3) substituted or unsubstituted cyclic alkyl groups having 4 to 6 carbons; and 4) substituted or unsubstituted aromatic groups having 4 to 10 carbons. The cyclic alkyl group and the aromatic group may contain one or more oxygen elements, sulfur elements, or nitrogen elements, and may be composed of two or more types of elements. Specific examples of the cyclic alkyl group having 4 to 6 carbons include a cyclobutyl group, a cyclopentyl group, a cyclohexyl group, a pyrrolidyl group, a tetrahydrofuranyl group, a tetrahydrothiophenyl group, a morpholyl group, a piperidyl group, and a tetrahydropyranyl group. Specific examples of the aromatic group having 4 to 10 carbons include a pyrrolyl group, a imidazoyl group, a oxazoyl group, a pyrazyl group, a pyrimidyl group, a furanyl group, a thiophenyl group, a pyridyl group, a phenyl group, an indoyl group, a benzoxazoyl group, a quinolyl group, an isoquinolyl group, a chromenyl group, and a naphthalenyl group. Examples of these substituents include fluorine atom, chlorine atom, a hydroxy group, an amino group, a cyano group, a nitro group, a trifluoromethyl group, a methyl group, an ethyl group, a propyl group, an isopropyl group, a methoxy group, an ethoxy group, a propoxy group, and an isopropoxy group.

The aromatic group having 4 to 10 carbons in the compound (I) may be a substituted or unsubstituted aromatic group; specific examples thereof include a pyrrolyl group, an imidazoyl group, an oxazoyl group, a pyrazyl group, a pyrimidyl group, a furanyl group, a thiophenyl group, a pyridyl group, a phenyl group, an indoyl group, a benzoxazoyl group, a quinolyl group, an isoquinolyl group, a chromenyl group, and a naphthalenyl group. Examples of these substituents include fluorine atom, chlorine atom, a hydroxy group, an amino group, a cyano group, a nitro group, a trifluoromethyl group, a methyl group, an ethyl group, a propyl group, an isopropyl group, a methoxy group, an ethoxy group, a propoxy group, and an isopropoxy group.

Examples of the pharmaceutically acceptable salt of a compound represented by the formula (I) in which $R^1$ is a hydroxy group include pharmaceutically acceptable metal salts, ammonium salts, and organic amine addition salts. Examples of the pharmaceutically acceptable metal salt include alkali metal salts such as lithium, sodium, and potassium salts, alkali earth metal salts such as magnesium and calcium salts, and metal salts such as aluminum and zinc salts; examples of the pharmaceutically acceptable ammonium salt include salts of ammonium and tetramethylammonium; and examples of the pharmaceutically acceptable organic amine salt include salts of triethylamine, piperidine, morpholine, and toluidine.

Among compounds represented by the formula (I), for example the above-described compounds represented by the formulas (A) to (C) are known compounds, and compounds in which $R^1$ is an alkoxy group can be obtained from the compound (A) by esterification by an ordinary method.

When it is desired to obtain a salt of a compound represented by formula (I), the compound (I) which is obtained in the form of a salt may be directly purified, and that which is obtained in free form may be dissolved or suspended in a suitable organic solvent, to which an acid is then added for the formation of the salt by a common method.

A compound represented by the formula (I) and a pharmaceutically acceptable salt thereof may be present in the form of addition products with water or various solvents; these addition products may also be used in the present invention.

The compound represented by the formula (I) used as the antimalarial drug of the present invention is not particularly limited provided that it is the compound (I); however, it is preferably a compound in which $R^2$ is a methyl group; $R^3$ is hydrogen; and $R^1$ is a hydroxy group (Alaremycin), a methoxy group, an ethoxy group, or an amino group (Primocarcin), particularly preferably a compound in which $R^1$ is a hydroxy group.

The compound (I) or a pharmaceutically acceptable salt thereof can be directly administered alone; however, they are typically preferably in the form of various pharmaceutical preparations, and the pharmaceutical preparations can each be produced by an ordinary pharmaceutical method by mixing the active ingredient with one or more pharmaceutically acceptable carriers.

Administration routes include oral administration or inhalation administration and parenteral administration such as intravenous administration.

Dosage forms include tablets and injections. The tablets may be produced according to an ordinary method by mixing various additives such as lactose, starch, magnesium stearate, hydroxypropylcellulose, polyvinyl alcohol, surfactant, and glycerin, and the inhalations may be produced according to an ordinary method, for example by adding lactose and the like. The injections may be produced according to an ordinary method by adding water, physiological saline, vegetable oil, solubilizer, preservative, and the like.

The effective dose and administration frequency of the compound (I) or a pharmaceutically acceptable salt thereof vary depending on the dosage form, the age, body weight, and symptom of a patient, and the like; however, administration is typically performed at a dose of 0.001 mg to 5 g, preferably 0.1 mg to 1 g, more preferably 1 to 500 mg per adult, once daily or several times daily in divided doses.

The present invention will be more specifically described below with reference to Examples. However, these Examples are not intended to limit the technical scope of the present invention.

EXAMPLE 1

Human red blood cells infected at an infection rate of 2% with ring-stage human malaria parasites were cultured in RPMI1640 medium containing AlbuMAX-II (Invitrogen) at 37° C. and a hematocrit of 4%. 50 μL of the culture was mixed with 50 μL of a medium containing Alaremycin to the concentrations shown in Table 1, to which [$^3$H]-hypoxanthine and [$^{14}$C]-isoleucine isoleucine were then added, followed by culture in a 96-well plate at 37° C. The repeat number was 2 for each concentration. After 25 hours, they were examined and the amount of β-rays released from [$^3$H]-hypoxanthine incorporated into a nucleic acid with de novo nucleic acid synthesis or from [$^{14}$C]-isoleucine incorporated into a protein with de novo protein synthesis was measured using a scintillation counter. The averages of the measured values were calculated, and the specific radioactivity incorporation was calculated by setting the measured value in the experiment for which Alaremycin was contained at a final concentration of 0.01 μM, to 100%. The results are shown in Table 1.

| Alaremycin Concentration (μM) | Specific Radioactivity Incorporation (%) | |
|---|---|---|
| | [³H]-Hypoxanthine | [¹⁴C]-Isoleucine |
| 0.01 | 100 | 100 |
| 0.1 | 100.4 | 93.3 |
| 1 | 92.8 | 88.8 |
| 5 | 84.8 | 84.7 |
| 10 | 66.8 | 64.8 |
| 50 | 2.8 | 3.6 |
| 100 | 1.5 | 2.1 |
| 200 | 1.1 | 1 |

As shown in Table 1, nucleic acid metabolism and protein synthesis in human malaria parasites were inhibited by Alaremycin in a concentration-dependent manner. The nucleic acid metabolism and the protein synthesis were inhibited to a nearly comparable extent by the same concentration of Alaremycin. Roughly, the radioactivity incorporation was inhibited nearly 50% by Alaremycin at a concentration of 15 μM and inhibited 95% or more by Alaremycin at a concentration of 50 μM. For both compounds of the formula (I) in which $R^1$ is a methoxy group and in which $R^1$ is an ethoxy group, the inhibition of nucleic acid metabolism and protein synthesis in human malaria parasites was measured according to the case of Alaremycin; as a result, although the inhibition of the nucleic acid metabolism and the protein synthesis was determined to be comparable for both of the compounds with the methoxy group and with the ethoxy group, the inhibition by Alaremycin was observed to be superior to that by these compounds.

EXAMPLE 2

Human red blood cells infected at an infection rate of 2% with ring-stage human malaria parasites were cultured in RPMI1640 medium containing AlbuMAX-II at 37° C. and a hematocrit of 4%. 50 μL of a medium containing Alaremycin or any of the other compounds shown in Table 2 was mixed with 50 μL of the culture to the indicated concentrations, to which [³H]-hypoxanthine was then added, followed by culture in a 96-well plate at 37° C. The repeat number was 2 for each concentration. After 25 hours, they were examined and the amount β-rays released from [³H]-hypoxanthine incorporated into a nucleic acid with de novo nucleic acid synthesis was measured using a scintillation counter. The averages of the measured values were calculated, and the specific radioactivity incorporation was calculated by setting the measured value in the experiment for which each compound is contained at a final concentration of 0.1 μM, to 100%. The results are shown in Table 2.

| Concentration (μM) | Alaremycin | Succinylacetone | 4,7-Dioxosebacic acid | 5-Aminolevulinic acid |
|---|---|---|---|---|
| 0.1 | 100 | 100 | 100 | 100 |
| 1 | 100.5 | 94.4 | 110.3 | 102.7 |
| 5 | 90.7 | 94.3 | 106.9 | 108.5 |
| 10 | 83.8 | 94.7 | 103.4 | 104.4 |
| 50 | 2.8 | 99.8 | 108 | 97.3 |
| 100 | 1.6 | 90.9 | 102.1 | 101.2 |
| 500 | Unadministered | 94.4 | 106.8 | Unadministered |
| 1000 | Unadministered | 88.6 | 100.1 | Unadministered |
| 5000 | Unadministered | 58.8 | 100 | Unadministered |
| 10000 | Unadministered | 21.4 | 97.1 | Unadministered |

As shown in Table 2, Alaremycin was observed to sufficiently inhibit nucleic acid metabolism in human malaria parasites in a significantly low concentration compared to compounds which have the similar skeleton, succinylacetone (SA: 4,6-dioxoheptanoic acid) and 4,7-dioxosebacic acid (DOSA). Alaremycin, SA, and DOSA are all inhibitors targeting 5-aminolevulinic acid dehydratase; however, the inhibitory activity thereof is known to vary depending on a target enzyme from the fine difference in the structure between target enzymes. These experimental results show that Alaremycin is particularly excellent as an inhibitor of 5-aminolevulinic acid dehydratase in human malaria parasites.

EXAMPLE 3

Tablets are prepared by an ordinary method using a composition of 10 mg of Alaremycin, 70 mg of lactose, 15 mg of starch, 4 mg of polyvinyl alcohol, and 1 mg of magnesium stearate (total 100 mg).

EXAMPLE 4

According to an ordinary method, distilled water for injection was added to a composition of 70 mg of Alaremycin, 50 mg of purified soybean oil, 10 mg of egg-yolk lecithin, and 25 mg of glycerin to a total volume of 100 mL, which was then filter-sterilized, followed by filling in a vial to prepare an injection.

INDUSTRIAL APPLICABILITY

The antimalarial drug comprising Alaremycin or a derivative thereof according to the present invention as an active ingredient can be used as a therapeutic and/or preventive agent for malaria.

The invention claimed is:
1. A method of treating or preventing malaria in a subject in need thereof, comprising administering to the subject Alaremycin or a derivative thereof represented by Formula (I),

Formula (I)

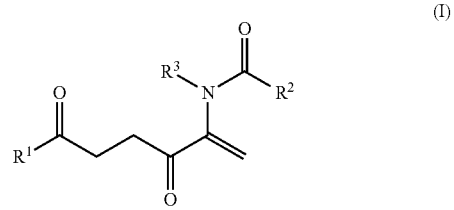

wherein $R^1$ represents a hydroxy group, an amino group, or a substituted or unsubstituted straight chain or branched alkoxy group or alkylamino group having 1 to 8 carbons; $R^2$ represents hydrogen, a substituted or unsubstituted straight chain or branched alkyl group having 1 to 8 carbons, or a substituted or unsubstituted aromatic group having 4 to 10 carbons; and $R^3$ represents hydrogen or a methyl group, or a pharmaceutically acceptable salt thereof, in an amount effective to treat or prevent malaria in the subject.

2. The method according to claim 1, wherein $R^1$ represents a hydroxy group; $R^2$ represents a methyl group; and $R^3$ represents hydrogen.

3. The method according to claim 1, wherein $R^1$ represents a methoxy group; $R^2$ represents a methyl group; and $R^3$ represents hydrogen.

4. The method according to claim 1, wherein $R^1$ represents an amino group; $R^2$ represents a methyl group; and $R^3$ represents hydrogen.

5. The method according to claim 1, in which the Alaremycin or derivative thereof is administered in a pharmaceutical preparation comprising a pharmaceutically acceptable carrier.

6. A method of treating or preventing malaria in a subject in need thereof, comprising administering to the subject a pharmaceutical preparation comprising Alaremycin or a derivative thereof as active ingredient and a pharmaceutically acceptable carrier, wherein the Alaremycin or a derivative thereof is represented by Formula (I), Formula (I)

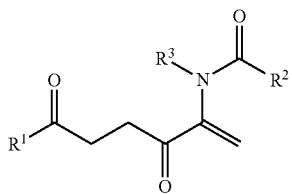

(I)

wherein $R^1$ represents a hydroxy group, an amino group, or a substituted or unsubstituted straight chain or branched alkoxy group or alkylamino group having 1 to 8 carbons; $R^2$ represents hydrogen, a substituted or unsubstituted straight chain or branched alkyl group having 1 to 8 carbons, or a substituted or unsubstituted aromatic group having 4 to 10 carbons; and $R^3$ represents hydrogen or a methyl group, or a pharmaceutically acceptable salt thereof, and wherein the preparation is administered in an amount effective to treat or prevent malaria in the subject.

7. The method according to claim 6, wherein $R^1$ represents a hydroxy group; $R^2$ represents a methyl group; and $R^3$ represents hydrogen.

8. The method according to claim 6, wherein $R^1$ represents a methoxy group; $R^2$ represents a methyl group; and $R^3$ represents hydrogen.

9. The method according to claim 6, wherein $R^1$ represents an amino group; $R^2$ represents a methyl group; and $R^3$ represents hydrogen.

10. The method according to claim 1, wherein the Alaremycin or derivative thereof is administered via a route selected from oral, inhalation, or parenteral.

11. The method according to claim 10, wherein the Alaremycin or derivative thereof is administered in tablet form or by injection.

12. The method according to claim 6, wherein the preparation is administered via a route selected from oral, inhalation, or parenteral.

13. The method according to claim 12, wherein the preparation is administered in tablet form or by injection.

* * * * *